(12) United States Patent
Gonzalez (10) Patent No.: US 9,915,639 B2
(45) Date of Patent: Mar. 13, 2018

(54) AGRICULTURAL DEVICE FOR RESTORING SOIL FERTILITY

(71) Applicant: Heriberto Bouza Gonzalez, Hialeah (FI)

(72) Inventor: Heriberto Bouza Gonzalez, Hialeah (FI)

( * ) Notice: Subject to any disclaimer, the term of this patent is extended or adjusted under 35 U.S.C. 154(b) by 286 days.

(21) Appl. No.: 14/645,303

(22) Filed: Mar. 11, 2015

(65) Prior Publication Data

US 2016/0029540 A1 Feb. 4, 2016

Related U.S. Application Data

(60) Provisional application No. 61/951,318, filed on Mar. 11, 2014.

(51) Int. Cl.
*A01B 49/02* (2006.01)
*G01N 33/24* (2006.01)
*A01B 61/04* (2006.01)
*A01B 13/08* (2006.01)
*G01N 37/00* (2006.01)

(52) U.S. Cl.
CPC ............ *G01N 33/24* (2013.01); *A01B 13/08* (2013.01); *A01B 61/046* (2013.01); *G01N 37/005* (2013.01); *G01N 2033/245* (2013.01)

(58) Field of Classification Search
None
See application file for complete search history.

(56) References Cited

U.S. PATENT DOCUMENTS

2010/0288518 A1* 11/2010 Reincke .............. A01B 45/023
172/21
2011/0024140 A1* 2/2011 De Bree .............. A01B 45/023
172/21

* cited by examiner

*Primary Examiner* — Tung Lau
(74) *Attorney, Agent, or Firm* — Albert Bordas, P.A.

(57) ABSTRACT

This agricultural device introduces an innovative approach to soil treatment that restores the fertility of depleted soils, which currently depend on chemical fertilizers to keep up with global food production needs. The new technology is based upon the concept of bioenergetics, whereby soil is conceived as the main factor that needs to be balanced in order to increase natural soil fertility, crop production, and food quality. This scientifically-based farming technology utilizes horizontal tillage—as opposed to conventional tillage—to reduce the entropy of the soil-plant-atmosphere system, helping regenerate biological memory and natural soil fertility. This new technology has been successfully tested on various kinds of terrains and crops, and its application progressively turns nature into the main factor of production equation, allowing us to reduce agrochemical dependency and production costs, and allowing us to overcome the apparent dichotomy that now exists between high food production needs and environmental care.

16 Claims, 9 Drawing Sheets

AGRICULTURAL DEVICE FOR RESTORING SOIL FERTILITY

BACKGROUND

The present invention is directed to an agricultural device that restores soil fertility. This innovation is based on a scientific concept that considers the entropic and bioenergetic balance as basic components of an advanced model of sustainable agricultural production which helps to feed the growing world population, in harmony with the environment. It is a new technology system consisting of a set of devices and methods for the ecological treatment of the soil, which has been proven in practice.

One of the most surprising mistakes we made in the history of mankind is not having understood quickly enough, the predominant role of entropy in the degradation and depletion of our soil.

The solution to the economic, energy and environmental crisis facing humanity is linked to the understanding of the connection at thermodynamic and quantum level, between economic growth, the increase of entropy, as well as, the regeneration processes of life and of raw materials in the soil-plant-atmospheric interactive system.

Entropy is a thermodynamic property whose formula is: $S=Q/T$, where S is the entropy, expressed in Kcal/K, the amount of heat Q exchanged Kcal and T the absolute temperature in degrees Kelvin at which heat is transferred.

Entropy is a measure of the amount of energy which is degraded in the form of heat and can never recover its ability to generate useful work. Soil richness and entropy vary inversely, so that when one increases the other decreases.

Man has tried to compensate the increase in the entropy of the soil by increasing the amount of chemical fertilizers applied. This technique is only a short-term solution, but in reality it only delays and worsens the problem supposedly intended to solve.

Soil is one of the most powerful forces of nature known to man, for it is where the mineral content is transformed into biological material. It is a primary force of nature with ability to transform the world.

Soil is a system whose components are minerals and living organisms, in which we find the key that determines the planet's ability to produce energy, food and raw materials necessary to sustain life.

This occurs by the transformation, at the ambient temperature and pressure, of the solar radiation, minerals and water, in biological energy.

Biological systems of land and sea are intimately connected and, through photosynthesis of plants, are the ones who have the ability to transform the electromagnetic waves from the sun into usable biological energy, all of which occur through natural processes highly efficient energy transfer in a quantum dimension.

When biological systems degrade and fail, the planet is disconnected, discharged and lose their ability to process and store energy from the sun, becoming an increasingly poorer place because of the increase of entropy.

Connectivity is a basic component of the structure of living systems. But when it is altered and degraded, it changes patterns of energy transport and feedback recycling operation, causing a kind of heat death of the system. This is what occurs in soils that lose their biological components, leaving only an inert substrate and becomes dependent on an external artificial source for operation.

The energy on the soil is passed from one to another living species, which act as transmission wires and transformers to ensure the biological process of energy recharge the planet, but the technologies used by conventional agriculture are destroying the biological capacity of the soil, which gradually becomes an empty, sterile container, which depends almost exclusively on the agrochemicals. Empty soils produce "empty foods" that become the hidden cause of many diseases.

The true potential of the soil fertility is not in its content of chemical elements, much less on the fallacy that the amount of fertilizer applied, but in its entropic ability to process and store energy.

Every year, worldwide, tens of millions of tons of fertilizer applied to agricultural soils in an attempt to increase their fertility. However, every day the world's soils are poorer and more dependent on chemicals, and as a result it is increasingly more costly to produce less. Note, that in order to produce each ton of nitrogen fertilizer over a ton and a half of oil equivalent needs to be consumed.

The enormous economic growth that mankind has achieved has taken place at the expense of the depletion of oil and other nonrenewable fossil fuels, which were formed by nature, from photosynthetic and microbiological processes of plants that lived millions of years ago.

As fossil fuels and other raw materials that we inherit from nature are exhausted, we are entering a new era in which economic growth will become more dependent on what we achieve in the farm fields.

Sustainable growth and future economic development cannot be achieved with solutions and raw materials of the past.

We must move from a model of economic growth based on the processing and consumption of existing raw materials to a model of economic growth based on technologies regeneration and transformation of new raw materials, where the soil will become the first link in productive chains and the main source of wealth.

Since 1934 Henry Ford could envision a future where essential fuels and raw materials for industrial development would be produced in the farmland and prophetic words of wisdom he declared as follows:

"I foresee the time when industry shall no longer denude the forests which require generations to mature, nor use up the mines which were ages in the making, but shall draw its raw material largely from the annual products of the fields. I am convinced that we shall be able to get out of the yearly crops most of the basic materials which we now get from forest and mine [Modern Mechanix (1934)]."

In soils of Amazonia, despite being regarded as low fertility, the lush green landscape of the planet was formed, without a single gram of fertilizer. However, when these soils are subjected to conventional agricultural management technologies they rapidly degrade and lose their productive capacities.

Stated in other words, is not a problem of lack of chemical fertilizers, it is a problem of biophysical and thermodynamic processes, which are regenerated by restoring energy balanceand entropy in the ground.

Plant nutrition is not as simple as the application and absorption of nutrients; it is a quantum interactive process of exchange of matter, energy and genomic information between plants and all living species that inhabit in the biosphere.

During my 40 years of research, I have been upgrading my technology based upon my discovery of an ecological method by which the entropy is reduced and the richness of the earth is regenerated. It is based on the disconnection and connection of the soil layers through which the anisotropic stratification is induced, which is essential to regenerate natural gradients of life and soil fertility, all of which allows capture and storage of energy and the reduction of entropy in the biosphere.

I found a way to achieve this by cutting the soil transversely to the force of gravity and the prevailing direction of the flow of energy on earth.

I designed a set of Aerodynamic Cutting Device (ACD), (FIG. 1, FIG. 2.1-2.4) to implement and structure in the most efficient way, an entropic system of sustainable agricultural technologies, all of which is the subject of the present invention.

The second law of thermodynamics states that energy always flows from a system or layer with high energy density to another system or layer with a lower energy density. This law is essential to the functioning of life in the soil and other components of the biosphere.

The impact of new technology in the induction of the formation of layers with different Bioenergetic density (anisotropic stratification), is the key to reducing the entropy, and regenerate the life and fertility of soils.

This method allows to gradually overcoming the serious disadvantage of conventional technologies, which depend on the increasing use of chemicals in food production, biofuels and other products that are essential to modern society. Through implementation and understanding of biological, quantum and thermodynamic principles behind it, unprecedented technological change will occur in the world's agricultural production.

The scientific basis and technological solution of the present invention are based on a revolutionary concept that recognizes thermodynamics and quantum nature of the biophysical processes involved in soil fertility, the productive potential of the land, and the entropy balance of the soil-plant-atmospheric system. It allows progressively reduction of dependence on agrochemicals in the production of food, biofuels and other commodities essential to the economy. The new technologies have been successfully tested in practice, and are comprised of a set of devices and methods for ecological soil treatment, which are able to reduce the entropy of the soil, by regulating the magnitude and intensity of propagation of energy through its layers. This is achieved by an Aerodynamic Cutting Device (ACD) which cuts the soil layers transversely to the force of gravity and the predominant direction of energy flow directions, which causes a cyclical process of disconnection and reconnection of the layers, and induce stratification and anisotropy indispensable to regenerate natural gradients of life and fertility in the soil. The system is further comprised of a novel Mechanism of Protection Against Obstacles (PMO) with automatic reverse, and a Versatile Agricultural Device (VAD) for multiple agricultural tasks, as well as, new more efficient Assembly Regulation, and shank Positioning Mechanism (ARPM), adjustable set up depending on task to be perform and arrangement of shanks, and the Integral Coupling Mechanism (ICM) to different types of tractors.

DRAWINGS

The present invention will be better understood from the detailed description given herein below and the accompanying drawings with which are given by way of illustration only:

FIG. 2.1-2.4 show how a side top and button view of Aerodynamic Cutting Devices (ACD) of the present invention, which are attached to each other;

WRITTEN DESCRIPTION

As seen in FIG. 1-9 of the drawings an agricultural device for restoring soil fertility is comprised of an Aerodynamic Cutting Device (ACD) that cuts the soil layers transversely to the predominant direction of energy flow. It has its own Protection Mechanism against Obstacles (PMO) with own auto return an efficient Assembly Regulation, and shank Positioning Mechanism (ARPM), along the crossbar 100. It contains an Versatile Agricultural Device (VAD) to perform multiple agricultural tasks, which include a mechanism for its regulation. It has an Integral Coupling Mechanism (ICM) for vertical and horizontal regulation, for different categories of tractors. It has a Multipurpose Device (MD) that performs multiple tasks such as, cut stubble and crop residues, buried irrigation hoses, transporting equipment by narrow roads, etc.

The Aerodynamic Cutting Device (ACD) (FIG. 1, FIG. 2.1-2.4) comprises of two circular plates 1 and 2 with different radii both with beveled edges 11 and 12 that are between 12 to 22 degrees respectively. The largest circular plate 1 and the lower circular plate 2 are non-concentrically way joined bottom—up though three screws 15, 16, 17, which are threaded into the triangular connector 3, and cross the circular plate 2 through three holes 21, 22 and 23. The front apex angle is approximately 18 to 21 degrees; and the lower plate 2 is positioned below of the beveled edge 11, and the larger plate 1 serves as structural basis for the fixing screw 13, 14 of the arch-shape connector 5, and two side blades 4, whose circular sector is defined by two perpendicular radii to each other, and are symmetrically positioned about the center, on both sides of the circular plate 1 and are fixed thereto by threaded connection 6, 7, 8 which cross the plate 1 through holes 118, 119 and 120, allows progressively extend the cutting width of the cut device.

Figure 1:
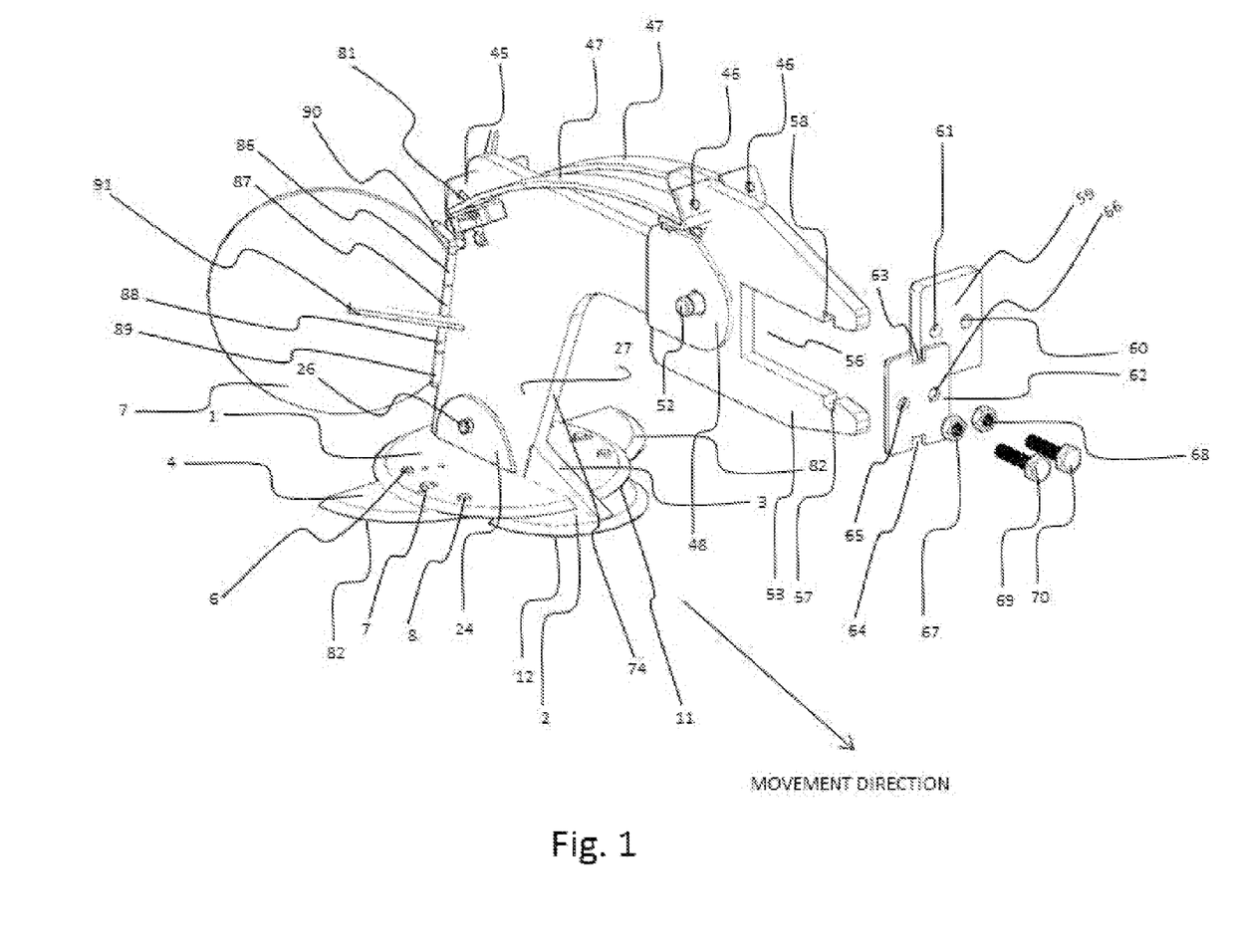
FIG. 1 shows a perspective side view of Aerodynamic Cutting Devices (ACD) with horizontal cutting blades of one of the embodiments of the present invention.
Figure 2:
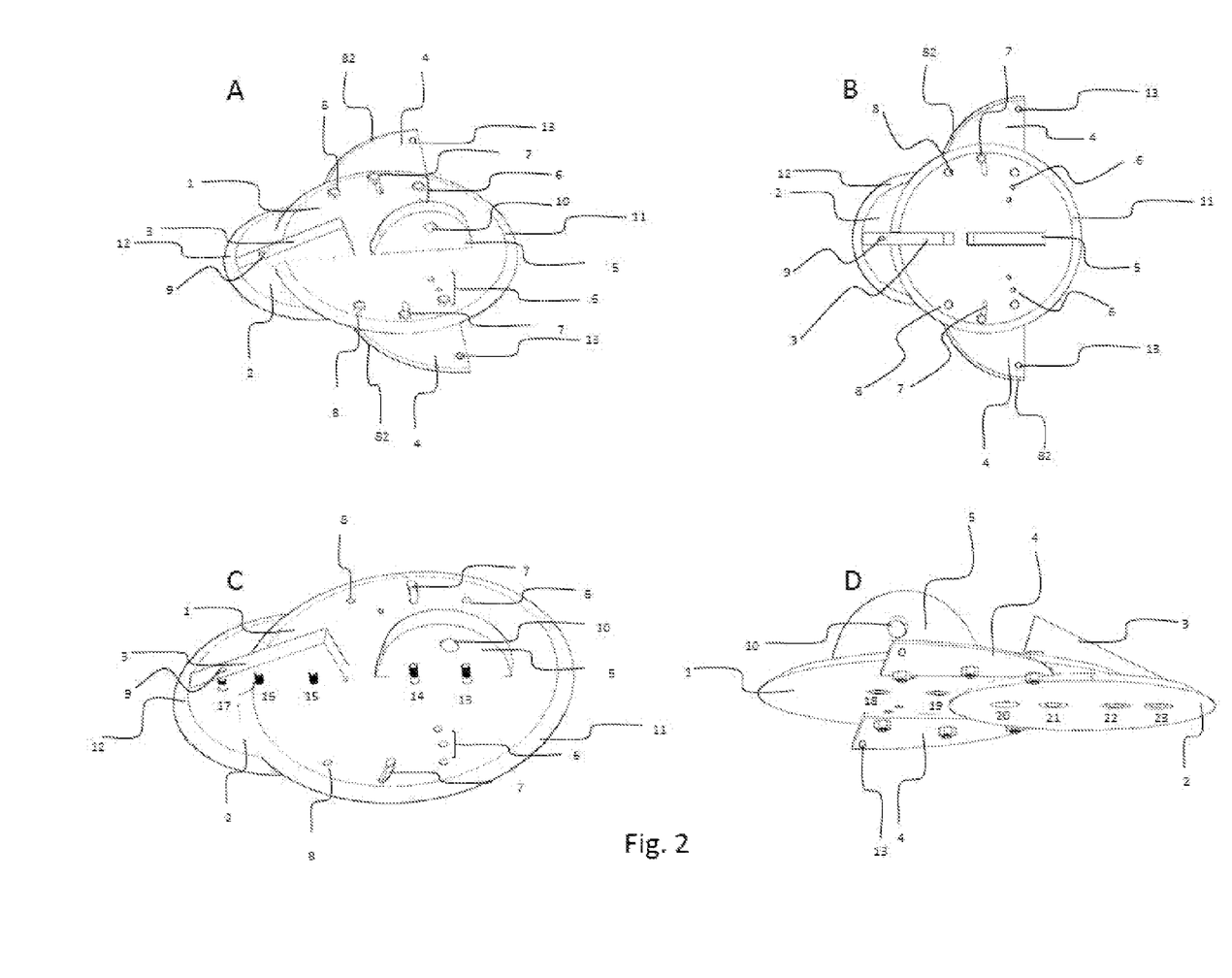
Figure 3:
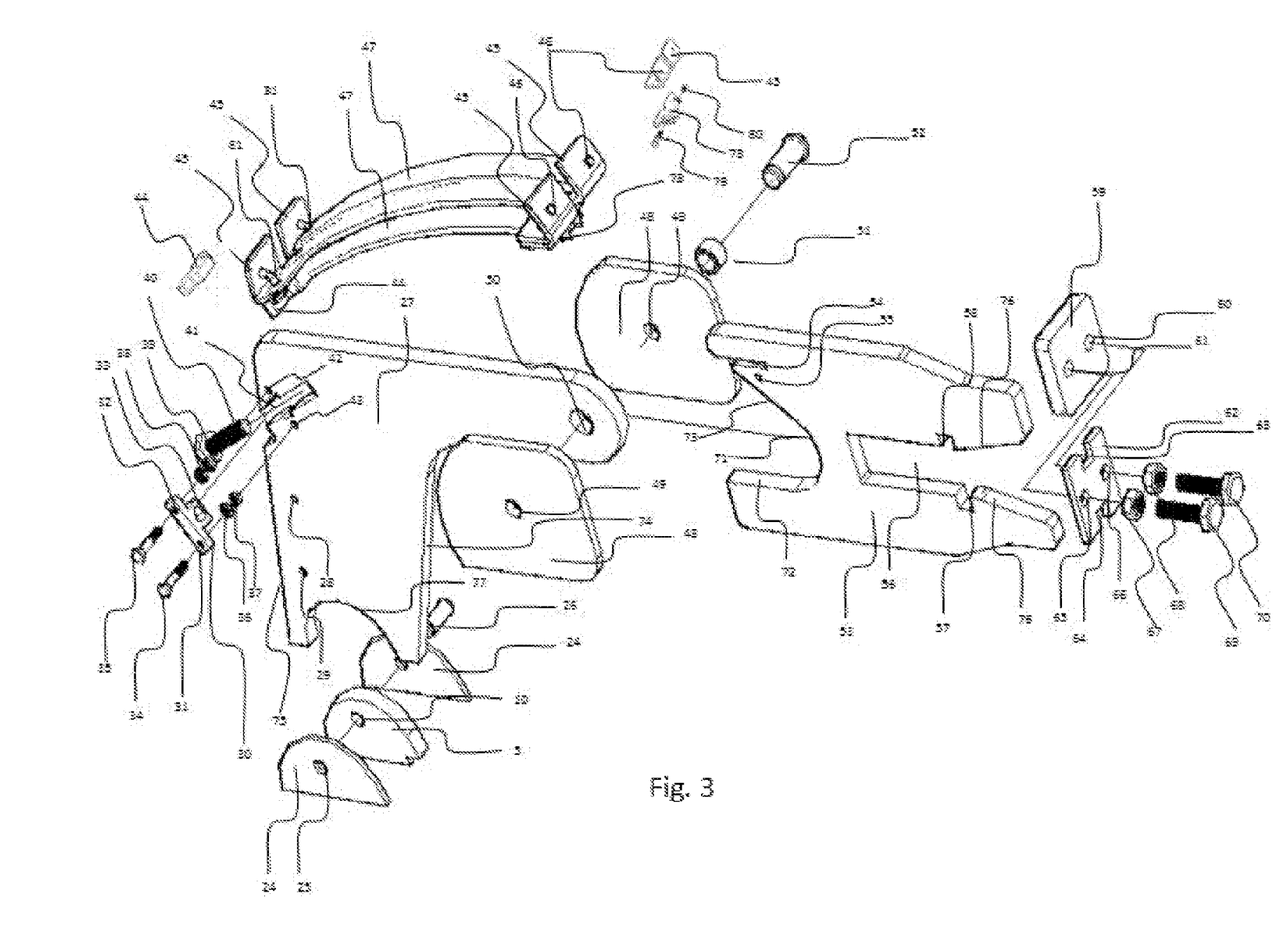
FIG. 3 shows a perspective exploded view of the rear mounting of the efficient Assembly Regulation, and shank Positioning Mechanism (ARPM), and others parts of the present invention that is used to mount the rear portion of the invention to a support bar.
Figure 4:
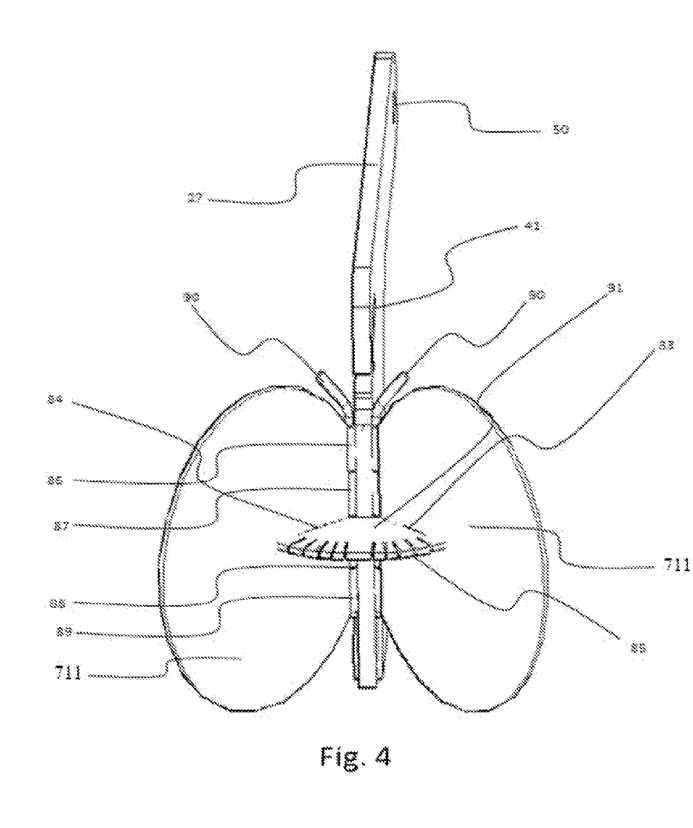
FIG. 4 shows a perspective rear view of the mounting Versatile Agricultural Device (VAD) of the present invention.
Figure 5:
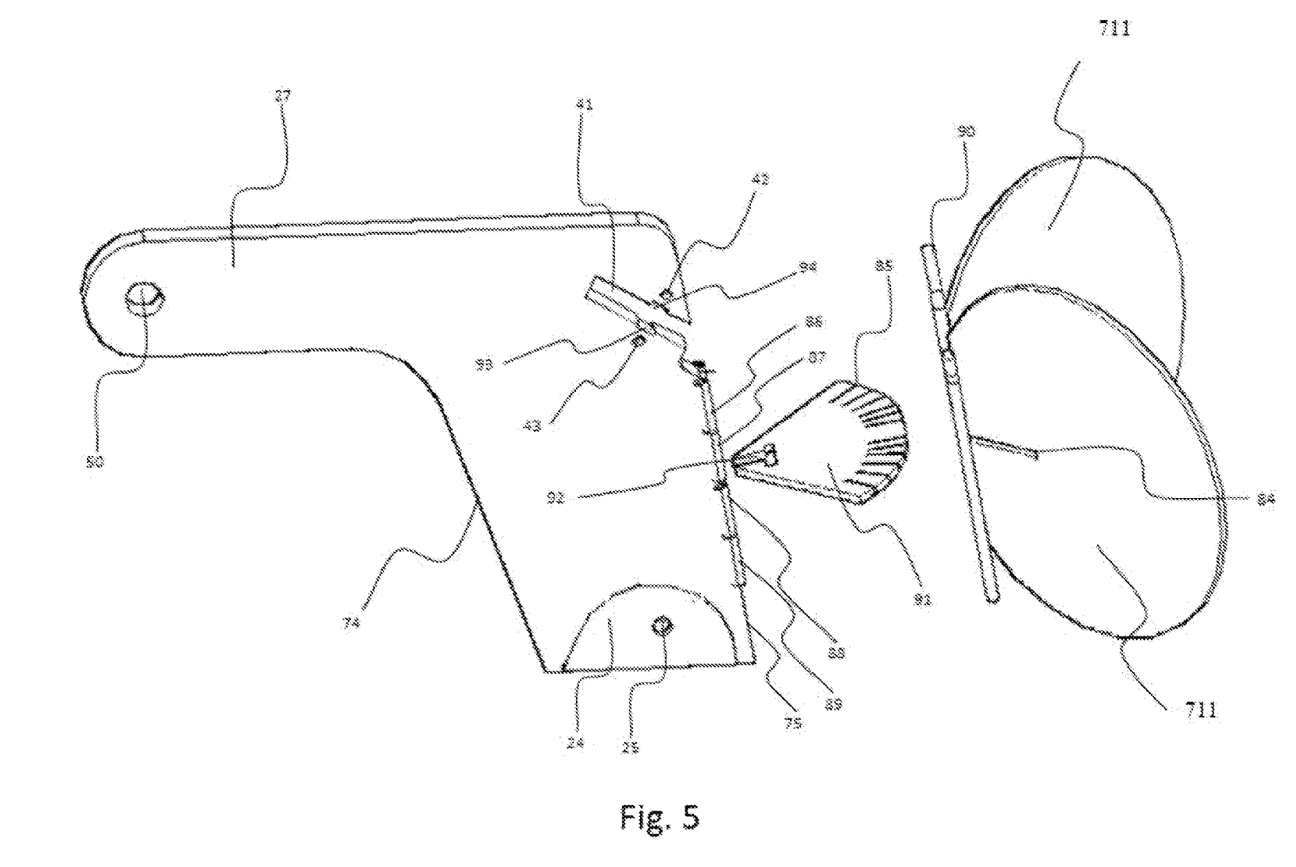
FIG. 5 shows a side exploded lateral rear view of the Versatile Agricultural Device (VAD)
Figure 6:
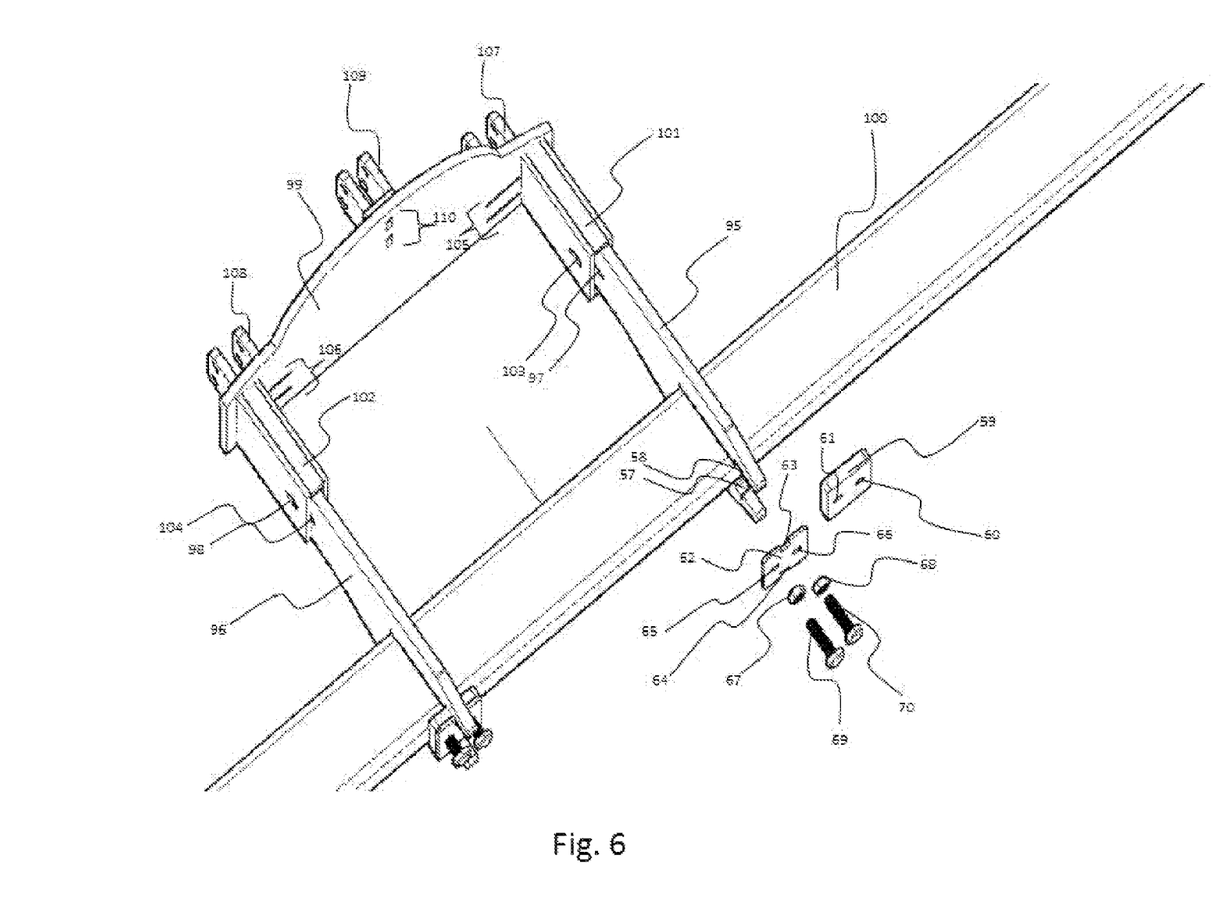
FIG. 6 shows a perspective view of a Integral Coupling Mechanism (ICM) that attaches the present invention to a tractor or any other towing vehicle.
Figure 7:
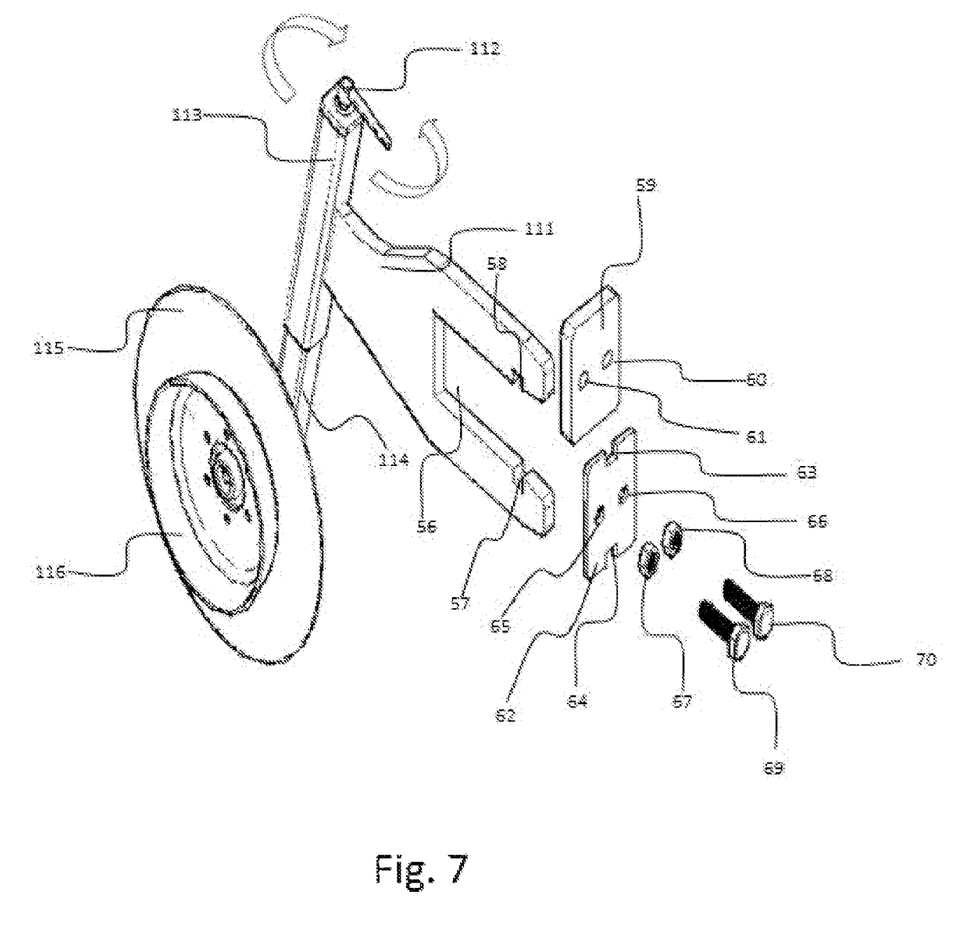
FIG. 7 shows a perspective view of a Multipurpose Device (MD) of the present invention.
Figure 8:
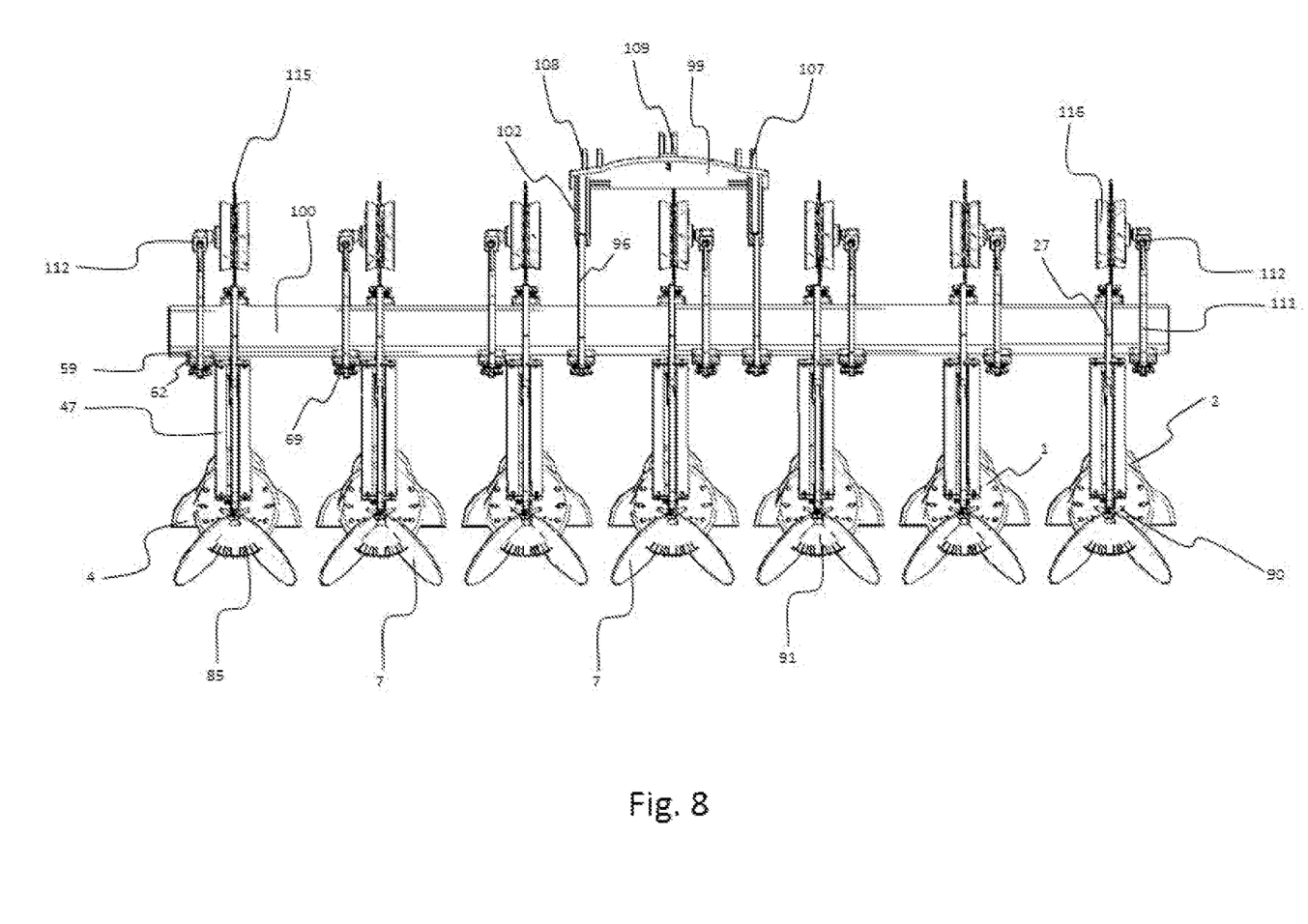
FIG. 8 shows a top view of one of the embodiments of the present invention.
Figure 9:
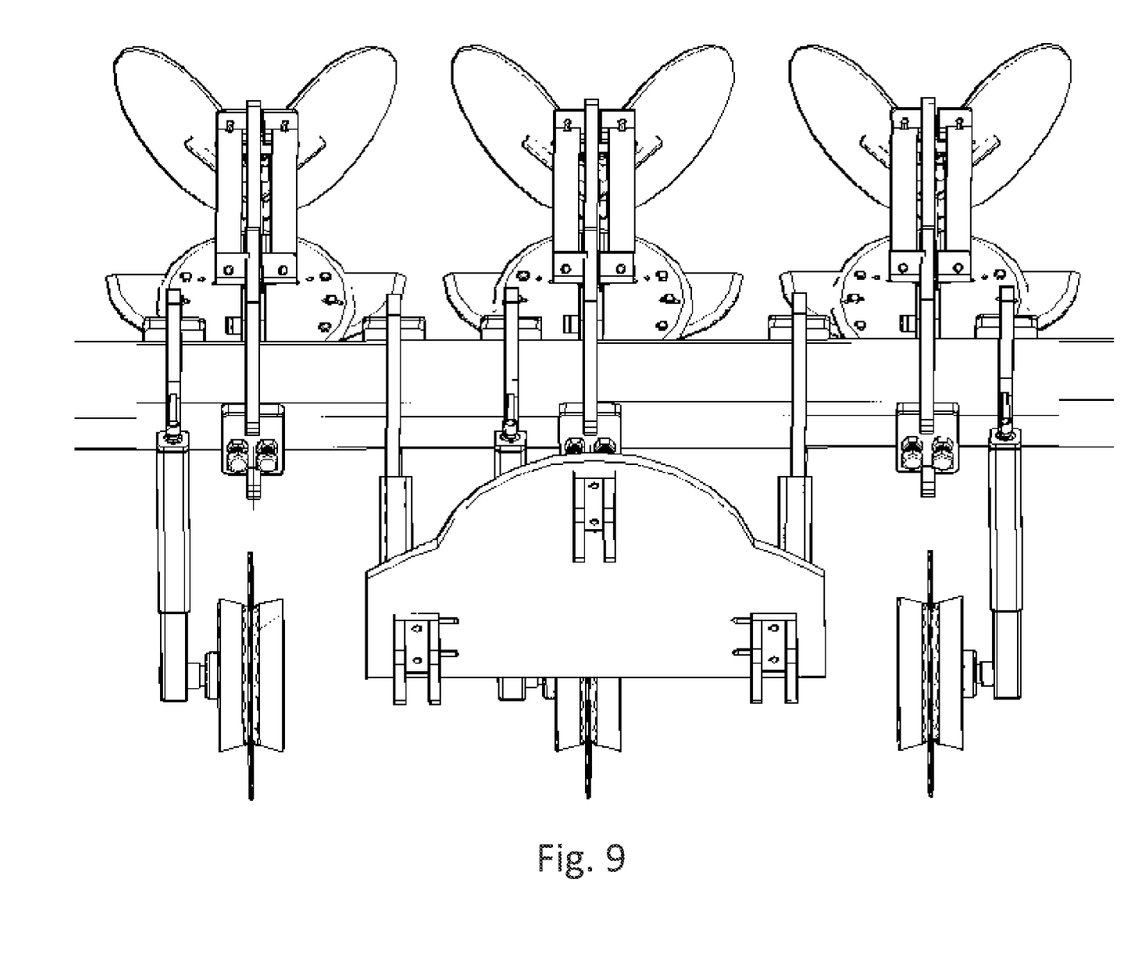
FIG. 9 is a top front perspective view of the embodiment shown in (FIG. 8).

In an embodiment of the Aerodynamic Cutting Device (ACD) described above, the radius of the larger or main circular plate 1, is approximately 1.6 times larger than the radius of the lower circular plate 2 while the radius of the side blades 4 and the radius main course 1 are approximately equal.

In another embodiment of the Aerodynamic Cutting Device (ACD) (FIG. 1, FIG. 2.1-2.4) of the present invention, the lower circular plate 2, is reversible, which means that once the circular 2 plate is worn by its use, the lower circular plate 2 can be rotated 180 degrees on its axis and start a new cycle, which can double its life.

In a further embodiment of the Aerodynamic Cutting Device (ACD) of the present invention, the side blades 4 are interchangeable, meaning they can be used either left or right side of the device. Besides these blades are foldable and can be regulated by a pivot mechanism that rotates around the front set screw 8, while the center screw 7 moves along a circular slot and the rear screw 6, is fixed by a holes chain describing a circular path. This allows to vary both the working width of the device, as well as, the lateral angle of cut, in order to reduce the degree of confrontation with obstacles, which optimizes the ability to dodge and reduces the power consumption of the tractor in very compact soil.

In another embodiment of the present invention, the device further comprises of a Protection Mechanism against Obstacles (PMO), (FIG. 1, FIG. 3 and FIG. 5) with automatic return, the protective mechanism comprises of a connecting arm 27, whose leading front edges 74, rear edge 75 are inclined with respect to the vertical 20 and 10 degrees respectively. The connecting arm 27 has at its lower end a bow-shaped housing 77 (FIG. 3) provided with two side protector covers 24, each of which has a hole 25 that are accommodated and screwed attachment point with the Aerodynamic Cutting Device (ACD)(FIG. 1, FIG. 2.1-2.4). The connecting arm 27 has a rear rectangular housing 41, at its upper end with two grooves 93, 94 (FIG. 5) and two holes 42, 43 in which a mechanism 30, 31, 32, 33, 35, 36, 37 is inserted. A tensor device 30, (FIG. 3), which has two equal tensor holes 32 positioned equidistantly with respect to the hole 33, the latter has an internal thread where the tensor screw 39 is introduced which serves for tensioning the impact protection mechanism. Tensor device 30, (FIG. 3) is part of the mechanism for adjusting the tension of the leaf springs 47 and engages via lateral sliding grooves 93 and 94 (FIG. 5) that are responsible for the whole burden, thereby being tightly fixed within the rectangular housing 41 and reinforced by tightening tensor screw 35, washer 36 and nut 37 respectively. The PMO further comprises two leaf springs 47, separated and housed in four V-shape support points 45, (two front and two rear) in a V shape. with an internal angle of 60 to 90 degrees. The two V-shapes support points 45 are welded to a rear support base 44 (FIG. 3), and slid ably coupled to the rear rectangular housing 41 of the connecting arm 27, along a path 40 degrees to the horizontal plan. The two front V-shapes support points 45, is slid ably coupled within a front rectangular housing 54, parallel to the horizontal plane, which is situated on the rear upper part of the central support device 53, the Assembly Regulation, and Shank Positioning Mechanism (ARPM) of the crossbar 100, and is also a locking screw 79, to fasten the said mechanism through a hole 55 fitted. The line connecting the rear support base 44, front support base 78, located at the ends of each leaf spring 47, the horizontal plane cuts forming an angle of approximately 17 degrees. Each leaf spring 47 has two central grooves 61 (FIG. 3) in the ends, which are situated close to its two supports and are traversed by a curved screw 81 which does not interfere with the rotation movement of the mechanism and acts as a safety system for cases extreme efforts. In the back of the connecting arm 27, two holes 28, 29 to secure Versatile Agriculture Device (VAD) for performing multiple farming, which performs tasks such as trenching, ridging, cover seeds, leveling, etc. The PMO works by hinge formed by the pivot point hole 50, the front end of the connecting arm 27, and the two holes 49, of the side covers 48, which are attached to the clamping (ARPM) by welding or screws.

In a further embodiment of the the Protection Mechanism against Obstacle (PMO) with automatic return, the line from the pivot point 50, to the forward point of the lower circular plate 2 forms an angle with the vertical of 17 about 22 degrees.

In an embodiment of the present invention, the Assembly Regulation, and Shank Positioning Mechanism (ARPM) on the crossbar 100 comprises of a central support device 53 which is set and bolted or welded to two side covers 48, with a hole 49 (FIG. 3), each forming a housing for the articulated connecting arm 27, which is the set and bolted or welded to two side covers 48, with a hole 49, each forming a housing for the articulated connecting arm 27, that supports the PMO. The housing is characterized in that its inner periphery has circular central portion 71, which allows rotation of the connecting arm 27, an upper straight portion 73, which serves as a stop for the rotational movement upwards and another lower straight portion 72, parallel to the horizontal plane, which serves as a stop for the recoil of PMO. The rotational movement of the connecting arm 27 covers an approximate range of 43-55 degrees to the horizontal plane.

In an embodiment of the present invention, the efficient arrangement for Assembly Regulation, and Shank Positioning Mechanism (ARPM) has a rear upper part a front rectangular housing 54 (FIG. 3), in parallel position to the horizontal plane and a hole 55, in its part less used to secure with hole 80, and the locking screw 79, the front support base 78, of the leaf springs 47.

In still a further embodiment of the present invention, the efficient arrangement for Assembly Regulation, and Shank Positioning Mechanism (ARPM) comprises of a central rectangular cavity 56, in a position parallel to the horizontal plane and which serves as housing to the crossbar 100, to facilitate this coupling the flat upper and lower slide 76, located in the front of the central support device 53, the angle with respect to the horizontal is about 20 degrees down. It also has a double internal inferior slot 57, internal superior slot 58 which allows the coupling by lateral displacement of the pressure plate 59, parallel to the horizontal direction. piece in the form of H-shaped piece 62, with double outer groove 63 to the front coupling and two central holes 65, through which two separate compressing screws 69, are coupled to serving to prevent lateral movement of the pressure plate 59 and oppressive (ARPM) to fix the crossbar 100 by compressing screws 69, against the crossbar 100, which are fastened by their respective locking nuts 68.

In another embodiment of the present invention, the Versatile Agricultural Device (VAD) comprises of two circular plates 70, the leading edge is straight with a rectangular slot 84 located at the center in a direction perpendicular to said edge, which has a length equal to ¼ of their diameter. Each of the circular plates 70 is fixed at the rear edge 75, the connecting arm 27, in a V-shape Plate with two vertical pins 90, which pass through four concentrically tubular aligned segments 86, 87, 88, 89 two of which 86, 89 are exterior and are fixed to the circular plate 70 and the two inner Tubular aligned segments 87, 88 are secured to the rear edge 75 of connecting arm 27.

In still another embodiment of the Versatile Agricultural Device (VAD), comprises of an adjustment mechanism, which consists of a V-shape Plate 91, which is formed by a sector of a circle bounded by two radii that are cut into perpendicular and has a T-shaped central housing 92 (FIG. 3), with a rectangular portion and another oval direction, whose length is equal to ⅓ of the radius. Said T-shaped central housing 92, allows the double coupling to connecting arm 27 and vertical pin 90, respectively. The rear edge of the V-shape Plate 91, owns through its circular perimeter, a set of equally spaced grooves each 85, of rectangular shape, they move towards the center of the V-shape Plate 91 to a distance equal to ¼ of its radius. This permits adjusting the gap between the circular plates 70, in a range of 0 to 90 degrees In yet another embodiment of the present invention, the ICM couples to different types of tractors through a system of vertical and horizontal adjustment, the ICM comprise of a front panel 99, which consists on each lower side end a double groove 105, 106 located in a position parallel to the horizontal plane, which are fixed by screw connection, the hitch 107, 108. The double groove 105, 106 (FIG. 3), allows the lateral displacement of the hitch 107, 108 to match the sidebars of the tractor hydraulic system, which allows for effective engagement with all types of tractors. In the top center two slots 110 (FIG. 6), separated and aligned perpendicular to the horizontal plane, in which is fixed by hitch 109, which is coupled to the third point of the tractor are located. This connection hitch 109 can scroll through the slots 110 in the vertical plane, which allows for effective coupling with tractors of any category In another embodiment of the ICM comprises of a front panel 99, in whose rear part are coupled by screws, two trunks 101, 102 located on both side ends, which are attached to two side arms 95, 96 by a telescopic mechanism with holes 97, 98, 103, 104 (FIG. 6), and screws to decrease or increase the distance between the convenience front panel 99, and the crossbar 100, which facilitates the location of multiple tools working in that space. The side arms 95, 96, are attached to the crossbar 100, by ARPM according to claim 10.

In another embodiment of the present invention, the multipurpose Device (MD) that allows for the cutting of debris and crop residues, buried irrigation hoses and transporting equipment for narrow gauge, comprises a central support 111, an internal telescopic bar 114, and endless screw 112, and a metal ring 116 for depth control, as well as a sharp flat disc 115 (FIG. 7), cutting the stubble remains and to prevent these from becoming entangled in the working bodies. The MD is fastened to the crossbar 100, by (ARPM) according to claim 10 and further serves to bury the hoses for drip irrigation systems. The MD hoses for drip irrigation systems. The MD also has the function of allowing the transportation of equipment by narrow roads, which is achieved by rotating 90 degrees internal telescopic bar 114 and replaces the sharp flat disc 115 (FIG. 7), and metal rings 116 for tires.

The Methods and Technologies used by the present invention are composed by:
A method to calculate the Entropic soil coefficient (Ks).
A method for calculating Entropic Soil Compaction Limits (ESCL).
A method for calculating the Entropic Soil Coefficient (Ks), which is a formula for determining the magnitude of the energy inputs required to achieve stratified anisotropic in the soil layers. This is vital to maintain the gradients and the bioenergetics flow that reduce the entropy of the soil-plant-atmosphere system, all of which is essential to maintain and regenerate soil fertility. The method comprises the following steps:

Calculation of Bioenergetic Potential of Soil (BPS) provides the basis for determining its Internal Entropic Soil Potential (IESP).

$$BPS = OM\,(\%) \times V(m^3/ha) \times \rho A(T/m^3)$$

Where:
(BPS): Biological Potential Soil in tons of biomass per unit area.
(OM): Content of Soil Organic Matter in %.
(V): Volume of soil in m³/ha.
($\rho A$): Bulk density of soil expressed in T/m³.

$$V = L(m) \times A(m) \times D(m).$$

Where to:
(L): Length in meters.
(A): Width in meters.
(D): Soil Depth in meters.
to express the energy value of BPS we consider:
the energy equivalent of 1 kg of biomass is 3,500 Kcal on the other hand 1 cal=4.18398 Joules
then we have:

$$1\ kg\ of\ biomass = 3.5 \times 10^6\ cal \times 4.18398\ joules/cal$$

$$1\ kg\ of\ biomass = 14.6 \times 10^6\ J$$

$$1\ Ton\ of\ Biomass = 14.6\ GJ$$

From which it follows $$(IESP) = BPS(T/ha) \times 14.6(GJ/T)$$

$$IESP = 14.6(GJ/T) \times OM\,(\%) \times V(m^3/ha) \times \rho A(T/m^3)\ \text{expressed in GJ/ha}$$

$$IESP = 14.6(GJ/T) \times OM\,(\%) \times V(m^3/ha) \times \rho A(T/m^3)\ \text{expressed in GJ/ha}$$

Where:
(IESP): Internal Entropic Potential of Soil expressed in GJ/ha.
Entropic soil coefficient (Ks) calculation:
the Entropic Soil Coefficient (Ks) is the constant of proportionality between the External Entropic Soil potential (EESP) and Internal Entropic Soil Potential (IESP). Its value expresses the quantity of input energy that can be assimilated by the edaphic metabolism system in each production cycle. This experimentally determined value is about 0.2. This is expressed by the formula:

$$Ks = EESP/IESP = 0.2$$

when the amount of energy incorporated into the soil in one growing cycle exceeds the value of Ks, the system is overloaded resulting in carbon loss and soil energy as heat is produced, while the opposite occurs when the system is depleted. In both cases an increase of entropy occurs, the efficiency of the process is reduced and forces a dependence on external inputs to the system. this effect is similar to what happens when a car battery alternator receives an amount of over or under load, causing a reduction in efficiency and lifespan.

The Entropic Soil Coefficient (Ks) is the constant of proportionality between the External Entropic Soil Potential (EESP) and Internal Entropic Soil Potential (IESP). Its value expresses the quantity of input energy that can be assimilated by the edaphic metabolism system in each production cycle. This experimentally determined value is about 0.2. This is expressed by the formula;

$$Ks = EESP/IESP = 0.2$$

When the amount of energy incorporated into the soil in one growing cycle exceeds the value of Ks, the system is overloaded resulting in carbon loss and soil energy as heat is produced, while the opposite occurs when the system is depleted. In both cases an increase of entropy occurs, the efficiency of the process is reduced and forces a dependence on external inputs to the system. This effect is similar to what happens when a car battery alternator receives an amount of over or under load, causing a reduction in efficiency and lifespan.

Another important method to calculate Entropic Soil Compaction Limits (ESCL).

The Entropic Soil Compaction Limits (ESCL) define the range of values expressed in soil compaction ton/m3, within which the maximum isometric stabilized biological energy flow through the soil for each crop is produced. These ranges are obtained from the determination of the Coefficient of Critical Soil Compaction (CCSC), whose value is a constant of proportionality between the Maximum Compaction (MC) and the Real Compaction (RC). Optimal for the development and yield of agricultural crops experimentally determined range, lies in the range of 0.76 to 0.86 approximately.

The present invention is also used for Eco-Entropic Cereal, Vegetables and Root Crops cultivation, which uses the Aerodynamic Cutting Device (ACD) by following these steps:

Calculate the amount of preceding crop biomass per hectare to be incorporated to the energy balance of the soil from the value of the Entropic soil coefficient (Ks), calculated according to the method explained in claim 17. With some exceptions, the calculation of the Ks must be done using the top 10 centimeters, which is the active layer of soil that is directly involved in the edaphic metabolism of ground biomass.

All biomass residues should be shredded on the surface to avoid interference with the subsequent work of preparation and planting. It should be avoided by all means mixing crop residues with the soil mass beyond 10 centimeters surface, as this will cause great loss of energy as heat, reduce the biological gradient and increases the entropy of the ground.

If residues of the previous crop or fallow exceed its Entropic Soil Coefficient (Ks), and the date of the next crop is sown immediately, they should be packaged for animal feed or other uses. Another alternative is to lengthen the time of preparation when planting is not immediate, in order to allow the edaphic metabolism balance the energy balance of the soil.

If the amount of biomass is lower than that established by Ks should be included in the rotation a crop such as corn or other cereal entropic balance to correct the soil by increasing the amount of carbon, which is the fuel that drives the machinery biological soil, similarly to the gas that drives the engine of an automobile.

Placing ACD on the crossbar 100 (FIG. 6, FIG. 8, FIG. 9) in a position parallel to the horizontal plane, for the total or localized soil preparation before planting. The ACD must be attached along the Cross bar 100 so that all are positioned on the same plane with respect to vertical.

The first task should preferably be done within 72 hours after harvest of the preceding crop. When surface biomass volumes are high, Multipurpose Device (MD) of the stubble are used, which are coupled to the front crossbar 100 and the center of each Aerodynamic Cutting Device (ACD). This prevents crop residues or weeds from tangling in the working bodies.

If there are lumps that might affect the quality of the seeding, these must be fragmented using a soil loosing roller, which can be coupled to the frame of the Aerodynamic Cutting Device (ACD), to accomplish both tasks in a single pass.

The elapsing time allowed between the first task and the time of planting should be 10 days or so, varying depending on the amount of weeds and the time required for irreversible wilting. If the soil is free of weeds and lumps, planting can be done immediately after the first task using a direct seeding machine for cereals.

For the case of vegetables or root crops are planted on ridges, the first pass of the VAD must be carried with attachments furrowed and hilling, which engage the rear edge of the connecting arm 27 and regulates the opening angle of the plates 70, as well as the location of the Aerodynamic Cut Device (ACD) to the distances required for each crop For vegetables and root crops that are planted on ridges covered with perforated polyethylene bands and using drip irrigation hoses buried; (ACD) are located on both sides of the grooves, and are regulated at a depth sufficient work to loosen and aerate the soil in raised beds from below, without affecting or hoses or polyethylene. This improves the physical properties of the soil, increases yields and extends the life of the irrigation facilities, avoiding the high costs to uninstall and reinstall hoses polyethylene bands.

For weed control and conservation of moisture after sowing, two lateral blades 4 are removed, using only the two circular plates 1 and 2, to till between the rows. Hilling is done by coupling the Versatile Agriculture Device (VAD) to the rear hole 28, 29 (FIG. 3) of the connecting arm 27. By setting it up this way, the Aerodynamic Cutting Device (ACD) can be used simultaneously, which allows performing both tasks in a singles pass.

Using this new technological system there will be a progressive reduction of 20% of the annual dose of chemical fertilizers and herbicides per year, to the point that, on the average, the application is no longer necessary after the fifth year of use of the technology. In cases where the soil is severely depleted or nutritionally imbalance and the soil pH must be corrected, rock powder must be apply superficially, without mixing it with lower soil layers.

The present invention is also useful in the technology to cultivate of Eco-Entropic pastures, which uses the Aerodynamic Cutting Device (ACD) down the following steps:

In grazing areas can present two main conditions: a) a method for rejuvenating pastures degraded by soil compaction, and invaded by woody weeds b) method for planting new grass.

The method for recovery and rejuvenation of degraded pastures is done during the spring or fall depending on the species established and the conditions of soil and climate. This method is carried out with the Aerodynamic Cutting Device (ACD) regulated to effect deep subsoil cut (20-30 centimeters), perpendicular to the taproots of woody weeds, in order to cut off the supply of water and nutrients and cause irreversible wilting. The deep cut allows for the top soil to remain intact, the grass roots not damaged and subsoil compaction (hardpan) eliminated, which creates favorable conditions for aeration, water storage and deep grass root growth.

The technology is recommended for all areas subject to direct livestock grazing and mechanized forage areas. In both cases the soils are exposed to strong compaction due to the heavy traffic of animals and machinery, especially considering that such activities are often performed with high moisture content in the soil.

When the Coefficient of Critical Soil Compaction (CCSC) reaches near its upper limit (0.86) values, it is the right time to make a pass with the Aerodynamic Cutting Device (ACD) at a depth of 20-30 cm. These conditions are generally in pasture every 1-3 years after the first pass made with the technology, depending on the soil management, pasture and grazing animal.

Is not recommended to move the animals to graze worked areas until the grass has reached a height of 20 centimeters. Also, do not allow a stay of cattle in the same pasture more than 72 hours, to avoid the damage of the new growth, and maintain a minimum height of grass equivalent to ⅓ of the initial height at the time of entry of the animals to grazing.

It is important to stress that the work to eliminate compaction on the total mass of the soil and to eliminate the taproots of the shrub weeds done at such a depth that the grass surface And root system remains virtually unchanged and conditions favorable for continued growth.

If the degree of deterioration of the pasture at the time of applying the method is very intense and bare grazing areas are presented, it is recommended that planting devices using direct sowing seeds of recommended species for each geographical area and for every season. This work should be performed after a pass with Aerodynamic Cutting Device (ACD), once it has occurred irreversible wilting of shrubby weeds.

Planting is done in two passes, distributing half the weight of seed per unit area on the first pass obliquely (45 degrees) to the path of Aerodynamic Cutting Device (ACD). The second pass of the planter is made perpendicular to the first direction, and distributes the remaining half of the seed. Finally roll ball is performed to improve the contact of grass seed with soil.

The method for sowing new pastures depends on soil conditions. For areas with heavy weed cover, a labor of pruning is done.

The progressive reduction of 20% of doses in cycles of annual crop of chemical fertilizers and herbicides is implemented, its application to dispense from the fifth year of use of technology. If required to do some work for liming soil pH correction at the beginning of the use of technology, this should be achieved by applying the product surface, without mixing with the lower soil layers.

It should be considered to apply nutrient rich natural rock powders to correct nutritional deficiencies for degraded and nutritionally imbalanced soils. This powder can be progressively converted into an assimilable form of nutrients for plants through soil biological activity.

The present invention is a Technology for Eco-Entropic Sugarcane cultivation, the application can be run in three different conditions: (a) method to renew established sugar cane plantations (b) method to regenerate and prolong the durability of the strains in established sugarcane plantations, (c) method to establish sugarcane plantations in rotation areas or fallow rotation In relation to section (a) to renew an established plantation of sugar cane, the following steps are performed as follows:

Immediately after harvesting sugarcane, using the residual moisture in the ground, the ball is made at the center of the strain with the Aerodynamic Cutting Device (ACD), following the same path of the previous furrow planting. Additionally, the Versatile Agricultural Device (VAD) must be attached to the back hole 28, of the connecting arm 27 for trenching, which must be regulated at an angle of 90 degrees, suitable for deep groove and with appropriate dimensions to place the seed at the bottom of it. Planting can be immediate and should be made as early as possible to avoid the loss of essential moisture for good germination of the seed.

The coupled Versatile Agricultural Device (VAD) performs the furrowing task and simultaneously allow in one pass, cut all the old plantation strain yolks and move them into the space between the rows, preventing it from falling into the groove and thus avoiding the mixing of old planting with the seed of the new variety to be sown.

Planting of the new stolons is done in conjunction with the same path of the previous stolons, which takes advantage of the best physical condition and the highest content of organic matter that has that area relative to spacing.

The distance between rows varies between 280 and 320 centimeters, depending on the conditions of soil, climate and crop varieties. If the distance between rows of the previous planting is 150 cm, the new planting is done only in alternate rows.

The stolon is placed with a scheme of planting 50-40-30, which means that the double cuttings 50 cm long are placed in parallel in the furrow 40 cm wide, at a distance of 30 cm. The sugar cane stolons are angled approximately 35 to 40 degrees with respect to the path of the groove. This allows for an approximate amount of 24 stolons per linear meter, whose spatial distribution in different planes perpendicular to the surface of the soil, prevents or minimizes the effect of self-shading and helps to mitigate the destructive action of the winds.

The bottom of the groove should not be completely flat, allowing cuttings rest lightly at the ends and left a volume of spongy ground, but with good contact below the seed to facilitate the abundant spread of the roots to the layers below, where the rain water or irrigation is stored.

The stolons should be covered with a thin layer of 5 cm of soil by loosening the soil of the slopes of the groove, whose work is also done with the same attachment, using VAD for cover the seed, which by coupled by bolted in holes located near the rear edge 75 of the connecting arm 27. The second work tape is after germination and bud clumps, leaving the ground level for mechanized harvesting time.

After sowing on the tillage implement the same are provided, placing the Aerodynamic Cutting Device (ACD) without the side blades, in the center of the row, for weed control and soil fluffy.

In relation to section (b) the method for regenerating and extending the durability of the strain is performed immediately after harvest double Aerodynamic Cutting Device (ACD) located on both sides of the strain at a distance of 40-50 cm from the center of the die to a depth of approximately 30-40 cm, lifting and turning off all of the strain subsoil to 5 centimeters apart, dropping again for communication and reconnection through a compactor metal ring 116 attached to the central rod pivotally, which also performs the function of regulating the depth of work together with the sharp flat discs 115 (FIG. 7), cut located front and center of each ACD.

The present invention discloses the Technology of Eco-Entropic Tree Orchards and Vineyards culture, which is applied in three conditions: a) New Orchards b) Mature orchards and c) Vineyards.

In relation to section (a) New orchards:

A pass using the Aerodynamic Cutting Device (ACD) is made in 30 centimeters deep fringes of 3 meters, so that the line of holes for transplanting trees, is situated at the center of said strip. The central portion of the distance between rows is maintained with natural vegetation until the work is completed planting, in order to facilitate the work of transfer and not stop the growth of the natural cover, whereby a live coverage is achieved thicker.

Once the transplanting of trees is completed, a pass with the Aerodynamic Cutting Device (ACD) is performed at varying depth of 30 centimeter in the center of the lane and 10 centimeters deep at 1 meter away from both sides of the tree line. This work aims to eliminate soil compaction, encourage deep root growth and encourage the formation of a mixed tapestry of green and life coverage, but dense enough to function as a natural reservoir of organic carbon, water and nutrients, all which helps to reduce the entropy of the soil and increase its natural fertility.

When natural vegetation between the rows of trees reach a height of 30 centimeters, a cutting is done with a lawn mower equipped with a deflector mechanism that throws the cut material toward the trunk of the tree rows, creating mulch that protects the soil from drying out, surface crusting and reduces the propagation of weeds. at the same time, such coverage becomes a source of slow release of nutrients and carbon to stimulate soil biological processes and plants.

In the first stage of implementation of the technology may require the application of herbicides in closer to the tree line area, but the dose is gradually reduced to make the mulch and loose soil, prevent weed growth.

It is further recommended that a intercropping on natural vegetation with legume species adapted to each climate zone, among which must be assessed Forage Peanuts (*Arachis pintoi*) and Canavalia (*Canavalia ensiformis*). This allows the diversification of the source of nutrients supplied by the coverage.

The above mentioned processes allows the regeneration of the natural fertility in the rows and in the tree lines before the roots extend into those areas. It is recommended that a progressive annual reduction of 20% of chemical fertilizers to achieve a balance between the nutrient demand of the crop and the rate of release of nutrients from organic mixed coverage. The annual number of passes of the Aerodynamic Cutting Device (ACD) depends on the value of the Entropic Soil Compaction Limit (ESCL), which is determined according to claim 18, while the number of cuts of vegetation cover depends on its growth rate. Practice shows that the two annual passes Aerodynamic Cutting Device (ACD) is sufficient to achieve a loose soil and healthy tapestry of natural vegetation between the rows of trees.

In relation to section (b) Mature Orchards:

Given that adult orchards subjected to conventional handling system generally follow a distorted and erratic root system development pattern, which occurs due to compaction and Entropic Soil Degradation, it is recommended that the first pass with the Aerodynamic Cutting Device (ACD) be initially performed less than 20 centimeters deep. Such work should be performed after completion of the harvest, with the goal of eliminating soil compaction and perform the progressive pruning of old roots.

Since Aerodynamic Cutting Device (ACD) has front and center sharp flat disks 115 (FIG. 7), to avoid tearing when pruning the old roots, achieving a clean, even cut to ensure regrowth of a new system root. When moving from one farm to another, it is necessary the disinfection of implements used Once regenerated and biological functioning of the garden is stabilized, its handling is done in line with the principles outlined in the previous section.

In relation to section (c) Grapevines:

Place the set of Aerodynamic Cutting Device (ACD) on the crossbar 100 in a position parallel to the horizontal plane, for the total or localized soil preparation before planting.

The ACD and MD must be attached along the rectangular bar so that all are positioned on the same plane with respect to the vertical.

The first pass should preferably be done within 72 hours after harvest of the preceding crop. When volumes of high surface biomass are high, the sharp flat disc 115 (FIG. 7), for cutting of stubble are used, which are coupled to the front crossbar 100 and the ACD.

The second pass is performed simultaneously by coupling both the Aerodynamic Cutting Device (ACD) and the Versatile Agricultural Device (VAD) for multiple tasks, which are positioned and fixed along the rectangular frame at a setting that matches the vid lines. This allows a single work leave traces planting furrows with a layer of soil removed to a depth of 40-50 centimeter in a swath 80 centimeter wide with a condition which is achieved optimum soil to plant vines.

after the planting, weed control and soil conditioning tasks are performed with three (ACD) spaced at a distance of 80 centimeters. Versatile Agricultural Device (VAD) is positioned front and center of each working Multipurpose Device (MD) that cut the remains and the crop residues.

after achieving a successful weed control, a live ground coverage should be established with a mixture of grasses and legumes short cycle adapted to the conditions of each area, which should be incorporated into the surface by cutting and grinding with a lawn mower with deflector mechanism to release part of the biomass to the planting line. Additionally, a thick layer of residue must be kept thick without mixing with the soil, to capture and conserve water and create an enabling environment for the biological activity of the soil and the gradual release of nutrient to the grapevine environment.

Chemical applications are expected to be reduced by approximately a 15 to 20% as the natural soil structure is regenerated and organic matter content rises, due to the changes in soil conditions due to the continuous use of this innovation.

While the invention is susceptible to various modification and alteration forms, specific embodiments thereof have been shown by way of example in the drawings and are herein described in detail. It should be understood, however, that the description herein of specific embodiments is not intended to limit the invention to the particular forms disclosed

| Glossary | |
|---|---|
| (ACD) | Aerodynamic Cut Devices |
| (PMO) | Protection Mechanism against Obstacle |
| (ARPM) | Assembly Regulation, and shank Positioning Mechanism |
| (VAD) | Versatile Agricultural Device |
| (ICM) | Integral Coupling Mechanism |
| (MD) | Multipurpose Device |
| (ESCL) | Entropic Soil Compaction Limits |
| (Ks) | Entropic Soil Coefficient |
| (BPS) | Bioenergetic Potential of Soil |
| (OM) | Organic Matter |
| (IESP) | Internal Entropic Soil Potential |
| (EESP) | External Entropic Soil Potential |
| (CCSC) | Coefficient of Critical Soil Compaction |
| (MC) | Maximum Compaction |

The invention claimed is:

1. An agricultural device for restoring soil fertility comprising a cutting device that cuts soil layers transversely to a predominant direction of energy flow, said cutting device comprises a protection mechanism against obstacles with a return having an assembly regulation and shank positioning mechanism along a crossbar, said cutting device further comprises an agricultural device comprising an integral coupling mechanism for vertical and horizontal regulation, and further comprising a device to cut stubble, crop residues, and buried irrigation hoses, and for transporting equipment;

further characterized in that said cutting device comprises first and second circular plates with different radii, said first and second circular plates have beveled edges that are between 12 to 22 degrees respectively;

further characterized in that said first and second circular plates are non-concentrically way joined bottom-up;

further characterized in that said first circular plate serves as a structural basis for an arch-shape connector and two side blades, whose circular sector is defined by two perpendicular radii to each other, and are symmetrically positioned about a center, both sides of said first circular plate are fixed by threaded connections that cross said first circular plate through holes to allow progressively extend a cutting width of said cutting device.

2. The agricultural device for restoring soil fertility set forth in claim 1, further characterized in that a first radius of said first circular plate is approximately 1.6 times larger than a second radius of said second circular plate while a radius of said side blades and said first radius of said first circular plate are approximately equal.

3. The agricultural device for restoring soil fertility set forth in claim 1, further characterized in that said side blades are interchangeable.

4. The agricultural device for restoring soil fertility set forth in claim 2, further characterized in that said second circular plate is reversible by rotating it 180 degrees on its axis.

5. The agricultural device for restoring soil fertility set forth in claim 3, further characterized in that said side blades are foldable and can be regulated by a pivot mechanism that rotates to vary both a working width of said cutting device as well as a lateral angle of cut, in order to reduce a degree of confrontation with obstacles to optimize an ability to dodge and reduce power consumption of a tractor in compact soil.

6. The agricultural device for restoring soil fertility set forth in claim 5, further characterized in that said protection mechanism against obstacles comprises a connecting arm whose leading front edges and rear edge are inclined with respect to a vertical 20 and 10 degrees respectively.

7. The agricultural device for restoring soil fertility set forth in claim 6, further characterized in that said connecting arm has at a lower end a bow-shaped housing with two side protector covers to accommodate an attachment point for said cutting device.

8. The agricultural device for restoring soil fertility set forth in claim 7, further characterized in that said connecting arm has a rear rectangular housing at its upper end with two grooves and two holes.

9. The agricultural device for restoring soil fertility set forth in claim 8, further characterized in that said protection mechanism against obstacles further comprises a tensor device, which has two equal tensor holes positioned equidistantly with respect to a hole having an internal thread where a tensor screw is introduced which serves for tensioning a impact protection mechanism, whereby said tensor device is part of a mechanism for adjusting tension of leaf springs and engages via lateral sliding grooves, thereby being tightly fixed within said rear rectangular housing and reinforced by tightening said tensor screw.

10. The agricultural device for restoring soil fertility set forth in claim 9, further characterized in that said leaf springs are separated and housed in four V-shape support points in a V shape with an internal angle of 60 to 90 degrees.

11. The agricultural device for restoring soil fertility set forth in claim 10, further characterized in that a first two of said four V-shapes support points are welded to a rear support base and slidably coupled to said rear rectangular housing of said connecting arm.

12. The agricultural device for restoring soil fertility set forth in claim 11, further characterized in that a second two of said four V-shapes support points are slidably coupled within a front rectangular housing, parallel to said horizontal plane, which is situated on a rear upper part of a central support device, and said assembly regulation and shank positioning mechanism of said crossbar.

13. The agricultural device for restoring soil fertility set forth in claim 12, further characterized in that said connecting arm secures an agriculture device for performing trenching, ridging, cover seeds, and leveling.

14. The agricultural device for restoring soil fertility set forth in claim 13, further characterized in that said protection mechanism against obstacles works by a hinge formed by a pivot point hole, a front end of said connecting arm, and two holes of said side covers that are attached to a clamp of said assembly regulation and shank positioning mechanism.

15. The agricultural device for restoring soil fertility set forth in claim 14, further characterized in that said protection mechanism against obstacles and a line from said pivot point to a forward point of said second circular plate forms an angle with a vertical of 17 about 22 degrees.

16. The agricultural device for restoring soil fertility set forth in claim 15, further characterized in that said assembly regulation and shank positioning mechanism on said crossbar comprises a central support device that is set and bolted or welded to two side covers with a hole, each forming a housing for articulating said connecting arm, which is set and bolted or welded to two side covers with a hole, each forming a housing for said articulated said connecting arm that supports said protection mechanism against obstacles.

* * * * *